(12) United States Patent
Tsudera et al.

(10) Patent No.: US 7,576,231 B2
(45) Date of Patent: Aug. 18, 2009

(54) METHOD FOR PRODUCING ISOCYANATE GROUP-CONTAINING SILOXANE COMPOUND

(75) Inventors: Takanobu Tsudera, Joetsu (JP); Tohru Kubota, Joetsu (JP); Ayumu Kiyomori, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 11/882,335

(22) Filed: Aug. 1, 2007

(65) Prior Publication Data

US 2008/0183001 A1 Jul. 31, 2008

(30) Foreign Application Priority Data

Aug. 1, 2006 (JP) .............................. 2006-209549

(51) Int. Cl.
C07F 7/10 (2006.01)
(52) U.S. Cl. ........................ 556/462; 556/414; 556/406; 556/460
(58) Field of Classification Search .................. 556/462, 556/414, 406, 460
See application file for complete search history.

(56) References Cited

U.S. PATENT DOCUMENTS

| 4,749,806 A | 6/1988 | Tkatchenko et al. |
| 5,886,205 A | 3/1999 | Uchida et al. |

FOREIGN PATENT DOCUMENTS

| DE | 102 40 388 A1 | 3/2001 |
| JP | 08104755 A * | 4/1996 |
| JP | 10-1486 A | 1/1998 |
| JP | 2001-26593 A | 1/2001 |
| JP | 2001-026593 A | 1/2001 |

OTHER PUBLICATIONS

European Search Report dated Nov. 14, 2007, issued in corresponding European Patent application No. 07 25 3013.
Database WPI Week 200136, Derwent Publications Ltd., London, GB, AN 2001-337802, XP002457180 & JP 2001 026593A.

* cited by examiner

*Primary Examiner*—Elvis O Price
(74) *Attorney, Agent, or Firm*—Westerman, Hattori, Daniels & Adrian, LLP.

(57) ABSTRACT

A method for producing an isocyanate group-containing siloxane compound is provided. In this method, a halogenated siloxane compound represented by the following general formula (1):

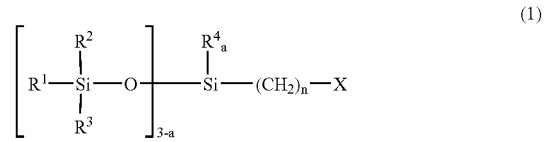

or the following general formula (2)

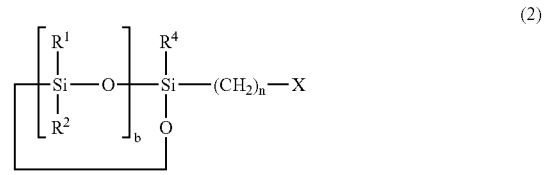

wherein $R^1$, $R^2$, $R^3$, and $R^4$ are independently hydrogen atom, a monovalent hydrocarbon group containing 1 to 8 carbon atoms, or a siloxy group represented by $OSiR^5R^6R^7$ wherein $R^5$, $R^6$, and $R^7$ are a monovalent hydrocarbon group containing 1 to 8 carbon atoms, X is a halogen atom, n is an integer of 1 to 10, a is 0, 1, or 2, and b is an integer of 2 to 9; is reacted with a cyanate salt represented by the following general formula (3):

$$M^{m+}(OCN)_m \qquad (3)$$

wherein M represents an alkali metal or an alkaline earth metal, and m is 1 or 2. The isocyanate group-containing siloxane compound produced is represented by the following general formula (4):

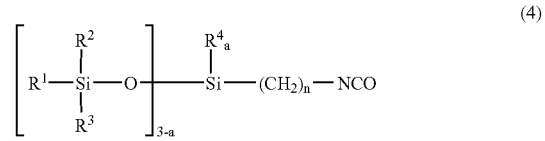

or the following general formula (5):

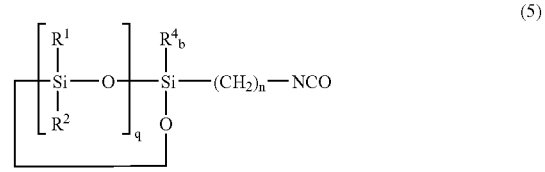

wherein $R^1$, $R^2$, $R^3$, $R^4$, n, q, and a are as defined above.

7 Claims, No Drawings

METHOD FOR PRODUCING ISOCYANATE GROUP-CONTAINING SILOXANE COMPOUND

CROSS-REFERENCE TO RELATED APPLICATION

This non-provisional application claims priority under 35 U.S.C. §119(a) on Patent Application No. 2006-209549 filed in Japan on Aug. 1, 2006, the entire contents of which are hereby incorporated by reference.

1. Technical Field

This invention relates to a method for producing an isocyanate group-containing siloxane compound.

2. Background Art

The isocyanate group-containing siloxane compound contains both isocyanate group and silicone group in the molecule. Since the isocyanate group readily reacts with a functional group having active hydrogen to form urethane bond and urea bond, the isocyanate group-containing siloxane compound is useful as a silicone modifying agent for an organic compound having active hydrogen.

The isocyanate group-containing siloxane compound has been produced, for example, by reacting an amino group-containing siloxane compound with a dialkyl carbonate to produce an alkyl carbamate, and thermally decomposing the alkyl carbamate (see, for example, Patent Document 1: JP-A 10-1486 and Patent Document 2: JP-A 2001-26593), or by reacting an amino group-containing siloxane compound with phosgene (see, for example, Patent Document 3: U.S. Pat. No. 3,584,024).

However, the method using the thermal decomposition of an alkyl carbamate is associated with the problems such as high price of the amino group-containing siloxane used for the starting material, incapability of producing the isocyanate group-containing siloxane compound at a low cost, and contamination of the product with the alkyl carbamate which failed to undergo thermal decomposition. The method using the phosgene also suffers from various problems such as the high price of the amino group-containing siloxane used for the starting material, incapability of producing the isocyanate group-containing siloxane compound at a low cost, and inadequateness of using the toxic and corrosive phosgene in commercial production.

DISCLOSURE OF THE INVENTION

In view of the situation as described above, an object of the present invention is to provide a high purity isocyanate group-containing siloxane compound at a low cost.

In order to obviate the situation as described above, the inventors of the present invention made an intensive study and found a method of reacting a halogenated siloxane compound with a cyanate salt. The present invention has been completed on the basis of such finding.

Accordingly, the present invention provides a method for producing an isocyanate group-containing siloxane compound. The method comprises reacting a halogenated siloxane compound represented by the following general formula (1):

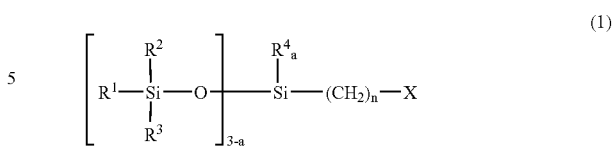

or the following general formula (2)

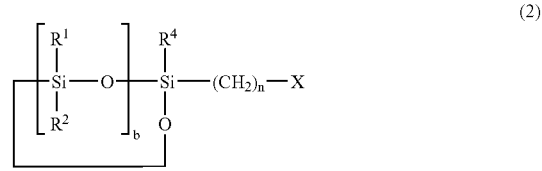

wherein $R^1$, $R^2$, $R^3$, and $R^4$ are independently hydrogen atom, a monovalent hydrocarbon group containing 1 to 8 carbon atoms, or a siloxy group represented by $OSiR^5R^6R^7$ wherein $R^5$, $R^6$, and $R^7$ are a monovalent hydrocarbon group containing 1 to 8 carbon atoms, X is a halogen atom, n is an integer of 1 to 10, a is 0, 1, or 2, and b is an integer of 2 to 9; with a cyanate salt represented by the following general formula (3):

$$M^{m+}(OCN)_m \qquad (3)$$

wherein M represents an alkali metal or an alkaline earth metal, and m is 1 or 2. The product is the isocyanate group-containing siloxane compound represented by the following general formula (4):

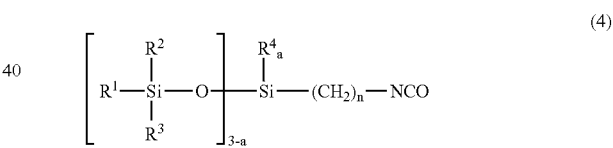

or the following general formula (5):

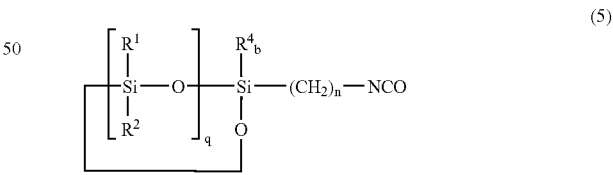

wherein $R^1$, $R^2$, $R^3$, $R^4$, n, q, and a are as defined above.

EFFECTS OF THE INVENTION

The production method of the present invention is capable of producing an isocyanate group-containing siloxane compound at a low cost by using an inexpensive starting materials, namely, a halogenated siloxane compound and a cyanate salt, and therefore, the method of the present invention has great industrial benefits.

DESCRIPTION OF THE PREFERRED EMBODIMENTS

The halogenated siloxane compound used for the starting material in the present invention is represented by the following general formula (1):

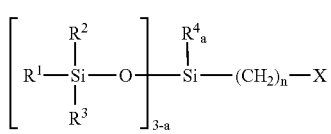 (1)

or the general formula (2):

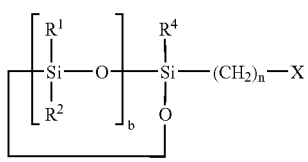 (2)

wherein $R^1$, $R^2$, $R^3$, and $R^4$ are independently hydrogen atom, a monovalent hydrocarbon group containing 1 to 8 carbon atoms, or a siloxy group represented by $OSiR^5R^6R^7$ wherein $R^8$, $R^6$, and $R^7$ are a monovalent hydrocarbon group containing 1 to 8 carbon atoms, X is a halogen atom, n is an integer of 1 to 10, a is 0, 1, or 2, and b is an integer of 2 to 9.

Exemplary monovalent hydrocarbon groups containing 1 to 8 carbon atoms represented by the $R^1$, $R^2$, $R^3$, $R^4$, $R^5$, $R^6$, and $R^7$ include alkyl groups such as methyl group, ethyl group, propyl group, and butyl group, cycloalkyl groups such as cyclopentyl group and cyclohexyl group, aryl groups such as phenyl group, alkenyl groups such as benzyl group, and alkenyl groups such as vinyl group and allyl group. The $R^1$, $R^2$, $R^3$, $R^4$, $R^5$, $R^6$, and $R^7$ may be either the same or different, and preferably, these groups are methyl group. Exemplary halogen atoms represented by X include chlorine, bromine, and iodine, and the preferred is chlorine. n is an integer of 1 to 10, and in particular, 1 to 6; a is 0, 1, or 2; and b is an integer of 2 to 9, and in particular, 2 to 4.

Among these, the preferred are the halogenated siloxane compounds represented by the general formula (6):

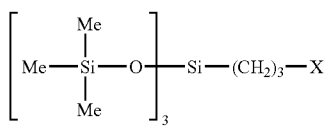 (6)

wherein X is as defined above, and Me represents methyl group.

The cyanate salt is represented by the general formula (3):

$$M^{m+}(OCN)_m \quad (3)$$

wherein M represents an alkali metal or an alkaline earth metal, and m is 1 or 2, and exemplary cyanate salts include lithium cyanate, sodium cyanate, potassium cyanate, rubidium cyanate, cesium cyanate, magnesium cyanate, calcium cyanate, strontium cyanate, and barium cyanate which may be used alone or in combination of two or more. More particularly, the cyanate salt is preferably sodium cyanate or potassium cyanate.

The cyanate salt is preferably used at 1 to 10 molar amount, and more preferably at 1 to 2 molar amount in relation to the halogenated siloxane compound. When used at an amount less than 1 molar amount, a certain proportion of the halogenated siloxane compound will remain unreacted, and use of the cyanate salt in excess of 10 molar amount may be uneconomical.

As described above, the halogenated siloxane compound and the cyanate salt are reacted in the method for producing the isocyanate group-containing siloxane compound of the present invention, and in such reaction, an aprotic polar solvent is preferably used for improving compatibility of the halogenated siloxane compound and the cyanate salt. Exemplary aprotic polar solvents include acetonitrile, dimethylformamide, N-methyl-2-pyrrolidinone, dimethyl sulfoxide, hexamethylphosphoramide, and diethylene glycol dimethyl ether, which may be used alone or in combination of two or more. More specifically, the preferred is use of dimethylformamide.

The aprotic polar solvent is preferably used at an amount of 10 to 200% by weight in relation to the halogenated siloxane compound. When used at an amount in excess of 200% by weight, complicated processing may be required in the post-treatment resulting in a reduced volumetric yield. When used at less than 10% by weight, reaction speed may become reduced to an industrially disadvantageous level.

In the present invention, the reaction is preferably carried out in the presence of at least one catalyst selected from phase transfer catalysts and metal iodide salts. Exemplary phase transfer catalysts include a quaternary onium salt, a crown ether, a cryptate, and the preferred are quaternary onium salts. The quaternary onium salt is represented by the following general formula (7):

$$(R_4Z)^+X^- \quad (7)$$

wherein R is a monovalent hydrocarbon group containing at least 1 to 40 carbon atoms, Z is phosphorus atom or nitrogen atom, and X is a halogen atom.

Exemplary quaternary onium salts include cetyltrimethylammonium chloride, tetrabutylammonium chloride, tetrapropylammonium chloride, tetrahexylammonium chloride, tetraheptylammonium chloride, tetrapentylammonium chloride, tetramethylammonium chloride, trioctylpropylammonium chloride, dodecyltrimethylammonium chloride, phenyltrimethylammonium chloride, hexadecyltrimethylammonium chloride, benzyltriethylammonium chloride, benzyltributylammonium chloride, benzyltrimethylammonium chloride, didodecyl dimethylammonium bromide, dimethyldioctadecylammonium bromide, cetyldimethylethylammonium bromide, tetraethylammonium bromide, tetraoctylammonium bromide, tetrabutylammonium bromide, tetrapropylammonium bromide, phenyltrimethylammonium bromide, benzyltrimethylammonium bromide, tetraethylammonium iodide, tetrabutylammonium iodide, ethyltriphenylammonium iodide, methyltriphenylammonium iodide, tetrabutylphosphonium chloride, triphenylbenzylphosphonium chloride, tetraphenylphosphonium chloride, hexadecyltributylphosphonium bromide, tetrabutylphosphonium bromide, trioctylethylphosphonium bromide, tetrabutylphosphonium iodide, and tetraphenylphosphonium iodide. These quaternary onium salts may be used either alone or in combination of two or more.

Examples of the metal iodide salt include lithium iodide, sodium iodide, potassium iodide, rubidium iodide, and cesium iodide, which may be used alone or in combination of two or more as a mixture. More specifically, the preferred is use of sodium iodide or potassium iodide.

Such catalyst is preferably used at an amount of 0.1 to 20% by mole, and more preferably at 1 to 10% by mole in relation to the halogenated siloxane compound. When used at an amount less than 0.1% by mole, reaction speed will be reduced to an industrially disadvantageous level, whereas the use in excess of 20% by mole may be uneconomical.

The reaction is preferably conducted by suspending the cyanate salt and the catalyst in a solvent, and adding the halogenated siloxane compound dropwise to the suspension. The reaction is preferably conducted in a non-oxidating atmosphere such as an inert gas atmosphere of nitrogen.

The reaction temperature of this reaction differs by the solvent selected. The reaction, however, may be carried out at a temperature in the range of from 0° C. to the boiling point of the reaction mixture generated by the reaction. More specifically, the reaction is preferably conducted at a temperature in the range of 30 to 150° C. Although the reaction time is not particularly limited, the reaction time is typically in the range of 1 to 30 hours.

If necessary, the production method of the present invention may further comprise other known steps such as pretreatment steps such as dehydration step, intermediate steps, and post-treatment steps such as purification step and recovery step.

EXAMPLES

Next, the present invention is described in further detail by referring to the Examples which by no means limit the scope of the present invention.

Example 1

A 500 ml flask equipped with a reflux condenser, a thermometer, and a dropping funnel was purged with nitrogen, and 26.0 g of potassium cyanate, 2.40 g of potassium iodide, and 100 g of dimethylformamide were placed in the flask. While stirring, 98.0 g of 3-chloropropyltris(trimethylsiloxy) silane was added dropwise at room temperature. After completing the addition, the reaction mixture was heated to 130° C. by heating the flask in an oil bath, and the reaction was allowed to proceed for 4 hours. After the completion of the reaction, the reaction mixture was cooled to room temperature, and the salt generated was separated by filtration.

A 300 ml distillation still equipped with a capillary, a thermometer, a vigrew column, and a condenser was purged with nitrogen, and the filtrate obtained as described above was placed in the flask. After reducing the pressure of the flask to 1.3 kPa and recovering the dimethylformamide, the pressure was reduced to 0.4 kPa, and the resulting product was collected by distillation. When the product was measured by gas chromatography, the resulting propyltris(trimethylsiloxy)silane 3-isocianate had a purity of 98.0% and the yield was 64.3%.

Example 2

A 500 ml flask equipped with a reflux condenser, a thermometer, and a dropping funnel was purged with nitrogen, and 26.0 g of potassium cyanate, 2.40 g of potassium iodide, and 100 g of dimethylformamide were placed in the flask. While stirring, 98.0 g of 3-chloropropyltris(trimethylsiloxy) silane was added dropwise at room temperature. After completing the addition, the reaction mixture was heated to 130° C. by heating the flask in an oil bath, and the reaction was allowed to proceed for 4 hours. After the completion of the reaction, the reaction mixture was cooled to room temperature, and 30 g of toluene and 150 g of water was added to dissolve the generated salt. The reaction mixture was then allowed to stand for 50 minutes, and the organic phase was collected.

A 300 ml distillation still equipped with a capillary, a thermometer, a vigrew column, and a condenser was purged with nitrogen, and the organic phase obtained as described above was placed in the flask. After reducing the pressure of the flask to 20 kPa and recovering the toluene, the pressure was reduced to 0.4 kPa, and the resulting product was collected by distillation. When the product was measured by gas chromatography, the resulting propyltris(trimethylsiloxy)silane 3-isocianate had a purity of 96.9% and the yield was 63.4%.

Example 3

A 500 ml flask equipped with a reflux condenser, a thermometer, and a dropping funnel was purged with nitrogen, and 42.7 g of potassium cyanate, 10.2 g of tetrabutylphosphonium iodide, and 200 g of dimethylformamide were placed in the flask. While stirring, 98.0 g of 3-chloropropyltris (trimethylsiloxy)silane was added dropwise at room temperature. After completing the addition, the reaction mixture was heated to 130° C. by heating the flask in an oil bath, and the reaction was allowed to proceed for 1 hour. After the completion of the reaction, the reaction mixture was cooled to room temperature, and the salt generated was separated by filtration.

A 300 ml distillation still equipped with a capillary, a thermometer, a vigrew column, and a condenser was purged with nitrogen, and the filtrate obtained as described above was placed in the flask. After reducing the pressure of the flask to 1.3 kPa and recovering the dimethylformamide, the pressure was reduced to 0.4 kPa, and the resulting product was collected by distillation. When the product was measured by gas chromatography, the resulting propyltris(trimethylsiloxy)silane 3-isocianate had a purity of 98.1% and the yield was 53.7%.

Example 4

A 100 ml flask equipped with a reflux condenser, a thermometer, and a dropping funnel was purged with nitrogen, and 2.6 g of potassium cyanate, 0.22 g of potassium iodide, and 10 g of dimethylformamide were placed in the flask. While stirring, 9.8 g of 3-chloropropyltris(trimethylsiloxy) silane was added dropwise at room temperature. After completing the addition, the reaction mixture was heated to 130° C. by heating the flask in an oil bath, and the reaction was allowed to proceed for 7 hours. When the reaction mixture was measured by gas chromatography, reaction rate of the propyltris(trimethylsiloxy)silane 3-isocianate was 99%.

Example 5

A 100 ml flask equipped with a reflux condenser, a thermometer, and a dropping funnel was purged with nitrogen, and 2.1 g of potassium cyanate, 0.45 g of tetrabutylphosphonium bromide, and 10 g of dimethylformamide were placed in the flask. While stirring, 4.9 g of 3-chloropropyltris(trimethylsiloxy)silane was added dropwise at room temperature.

After completing the addition, the reaction mixture was heated to 130° C. by heating the flask in an oil bath, and the reaction was allowed to proceed for 1.5 hours. When the reaction mixture was measured by gas chromatography, reaction rate of the propyltris(trimethylsiloxy)silane 3-isocianate was 94%.

Example 6

A 100 ml flask equipped with a reflux condenser, a thermometer, and a dropping funnel was purged with nitrogen, and 2.4 g of potassium cyanate, 0.24 g of potassium iodide, and 16.2 g of dimethylformamide were placed in the flask. While stirring, 9.8 g of chloromethyltris(trimethylsiloxy)silane was added dropwise at room temperature. After completing the addition, the reaction mixture was heated to 130° C by heating the flask in an oil bath, and the reaction was allowed to proceed for 6 hours. When the reaction mixture was measured by gas chromatography, reaction rate of the chloromethyltris(trimethylsiloxy)silane was 99%.

Example 7

A 100 ml flask equipped with a reflux condenser, a thermometer, and a dropping funnel was purged with nitrogen, and 2.5 g of potassium cyanate, 0.25 g of potassium iodide, and 16.9 g of dimethylformamide were placed in the flask. While stirring, 9.8 g of chloromethylheptamethylcyclotetrasiloxane was added dropwise at room temperature. After completing the addition, the reaction mixture was heated to 130° C. by heating the flask in an oil bath, and the reaction was allowed to proceed for 3 hours. When the reaction mixture was measured by gas chromatography, reaction rate of the chloromethylheptamethylcyclotetrasiloxane was 99%.

Example 8

A 100 ml flask equipped with a reflux condenser, a thermometer, and a dropping funnel was purged with nitrogen, and 2.3 g of potassium cyanate, 0.23 g of potassium iodide, and 15.6 g of dimethylformamide were placed in the flask. While stirring, 9.8 g of 3-chloropropylheptamethylcyclotetrasiloxane was added dropwise at room temperature. After completing the addition, the reaction mixture was heated to 130° C. by heating the flask in an oil bath, and the reaction was allowed to proceed for 2.5 hours. When the reaction mixture was measured by gas chromatography, reaction rate of the 3-chloropropylheptamethylcyclotetrasiloxane was 100%.

Japanese Patent Application No. 2006-209549 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A method for producing an isocyanate group-containing siloxane compound comprising the step of reacting a halogenated siloxane compound represented by the following general formula (1):

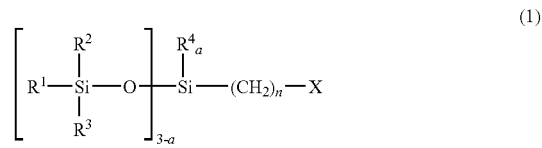

or the following general formula (2)

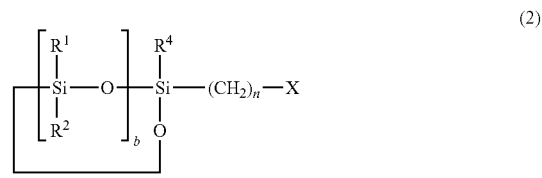

wherein $R^1$, $R^2$, $R^3$, and $R^4$ are independently hydrogen atom, a monovalent hydrocarbon group containing 1 to 8 carbon atoms, or a siloxy group represented by $OSiR^5R^6R^7$ wherein $R^5$, $R^6$, and $R^7$ are a monovalent hydrocarbon group containing 1 to 8 carbon atoms, X is a halogen atom, n is an integer of 1 to 10, a is 0, 1, or 2, and b is an integer of 2 to 9; with a cyanate salt represented by the following general formula (3):

wherein M represents an alkali metal or an alkaline earth metal, and m is 1 or 2; in the presence of a metal iodide salt to produce the isocyanate group-containing siloxane compound represented by the following general formula (4):

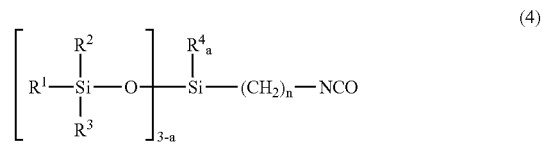

or the following general formula (5):

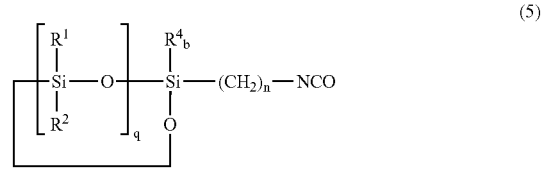

wherein $R^1$, $R^2$, $R^3$, $R^4$, n, b, and a are as defined above.

2. The method for producing an isocyanate group-containing siloxane compound according to claim 1 wherein the halogenated siloxane compound is the one represented by the general formula (6):

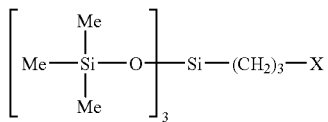 (6)

wherein X is as defined in formula (1), and Me represents methyl group.

3. The method for producing an isocyanate group-containing siloxane compound according to claim 1 wherein the cyanate salt is sodium cyanate or potassium cyanate.

4. The method for producing an isocyanate group-containing siloxane compound according to claim 1 wherein the reaction is conducted in an aprotic polar solvent.

5. The method for producing an isocyanate group-containing siloxane compound according to claim 1 wherein the metal iodide salt is sodium iodide or potassium iodide.

6. The method for producing an isocyanate group-containing siloxane compound according to claim 1 wherein the halogentated siloxane compound starting material is represented by the general formula (2) and the isocyanate group-containing compound is represented by the general formula (5).

7. The method for producing an isocyanate group-containing siloxane compound according to claim 1 wherein the halogentated siloxane compound starting material is represented by the general formula (1) and the isocyantate group containing compound is represented by the general formula (4).

* * * * *